United States Patent [19]

Randazzo

[11] Patent Number: 6,083,742
[45] Date of Patent: Jul. 4, 2000

[54] MAMMALIAN DEEP ORANGE NUCLEOTIDES

[75] Inventor: Filippo M. Randazzo, Emeryville, Calif.

[73] Assignee: Chiron Corporation, Emeryville, Calif.

[21] Appl. No.: 08/904,452

[22] Filed: Jul. 31, 1997

Related U.S. Application Data

[60] Provisional application No. 60/022,988, Aug. 2, 1996, provisional application No. 60/030,337, Nov. 5, 1996, and provisional application No. 60/045,886, Apr. 30, 1997.

[51] Int. Cl.$^7$ .......................... C12N 15/12; C12N 15/11; C07H 21/04; C07H 21/02
[52] U.S. Cl. ...................................... 435/320.1; 536/23.5
[58] Field of Search .................................. 536/23.1, 23.5, 536/24.1; 435/320.1, 69.1; 530/350

[56] References Cited

PUBLICATIONS

Shestopal, S.A. Database PIR, Accession No. S54252, Jul. 1995.
Hassouna, N. et al. Database Genbank, Accession No. X00525, Mar. 1991.
Marra, M. et al. Database Genbank, Accession No. W89460, Sep. 1996.
Marra, M. et al. Database Genbank, Accession No. AA111260, Nov. 1996.
Ausubel, F.M. et al. Current Protocols in Molecular Biology. John Wiley & Sons, New York, pp. 16.4.1–16.5.6, 1990.
Sato et al., "Homoeosis in Drosophila: A New Enhancer of Polycomb and Related Homoeotic Mutations" *Genetics* 105:357–370, Oct., 1983.
Kennison and Tamkun, "Dosage–Dependent Modifiers of Polycomb and Antennapedia Mutations in Drosophila" *Proc. Natl. Acad. Sci. USA* 85:8136–8140, Nov., 1988.
Lewin, "Commitment and Activation at Pol II Promoters: A Tail of Protein–Protein Interactions" *Cell* 61:1161–1164, Jun., 1990.
Paro, "Imprinting a Determined State into the Chromatin of Drosophila" *TIG* 6(20):416–421, Dec., 1990.
Goebl, "The bmi–1 and mel–18 Gene Products Define a New Family of DNA–Binding Proteins Involved in Cell Proliferation and Tumorigenesis" *Cell* 66:623, Aug., 1991.
Brunk et al., "Drosophila Genes Posterior Sex Combs and Suppressor Two of Zeste Encode Proteins With Homology to the Murine bmi–1 Oncogene" *Nature* 353:351–353, Sep., 1991.
van Lohuizen et al., "Sequence Similarity Between the Mammalian bmi–1 Proto–Oncogene and the Drosophila Regulatory Genes Psc and Su(z) 2" *Nature* 353:353–355, Sep., 1991.
DeCamillis et al., "The Polyhomeotic Gene of Drosophila Encodes a Chromatin Protein that Shares Polytene Chromosome–Binding Sites with Polycomb" *Genes and Development* 6:223–232, 1992.
Felsenfeld, "Chromatin as an Essential Part of the Transcriptional Mechanism" *Nature* 355:219–224, Jan., 1992.
Sinclair et al., "Genetic Analysis of the Additional Sex Combs Locus of *Drosophila Melanogaster*" *Genetics* 130:817–825, Apr., 1992.
Travers, "The Reprogramming of Transcriptional Competence" *Cell* 69:573–575, May, 1992.
Djabali et al., "A Trithorax–Like Gene is Interrupted by Chromosome 11q23 Translocations in Acute Leukaemias" *Nature Genetics* 2:113–118, Oct., 1992.
Gu et al., "The t(4;11) Chromosome Translocation of Human Acute Leukemias Fuses the ALL–1 Gene, Related to *Drosophila trithorax*, to the AF–4 Gene" *Cell* 71:701–708, Nov., 1992.
Tkachuk et al., "Involvement of a Homolog of Drosophila Trithorax by 11q23 Chromosomal Translocations in Acute Leukemias" *Cell* 71:691–700, Nov., 1992.
Winston and Carlson, "Yeast SNF/SWI Transcriptional Activators and the SPT/SIN Chromatin Connection" *TIG* 8(11):387–391, Nov., 1992.
Barba et al., "HOX Gene Expression in Human Cancers" *Advances in Nutrition and Cancer,* Zappia et al., Eds., Plenum Press, N.Y., pp. 45–57, 1993.
Cillo, "Hox Genes in Human Cancers" *Invasion Metastasis* 14:38–49, 1994–1995.
Moehrle and Paro, "Spreading the Silence: Epigenetic Transcriptional Regulation During Drosophila Development" *Developmental Genetics* 15:478–484, 1994.
Kennison, "Transcriptional Activation of Drosophila Homeotic Genes from Distant Regulatory Elements" *TIG* 9(3):75–79, Mar., 1993.
van der Lugt et al., "Posterior Transformation, Neurological Abnormalities, and Severe Hematopoietic Defects in Mice with a Targeted Deletion of the bmi–1 proto–oncogene" *Genes and Development* 8:757–769, 1994.
Denis and Green, "A Novel, Mitogen–Activated Nuclear Kinase is Related to a Drosophila Developmental Regulator" *Genes and Development* 10:261–271, 1996.
Epstein, "Polycomb and Friends" *BioEssays* 14(6):411–413, 1992.
Chiba et al., "Two Human Homologues of *Saccharomyces cerevisiae* SW12/SNF2 and *Drosophila brahma* are Transcriptional Coactivators Cooperating with the Estrogen Receptor and the Retinoic Acid Receptor" *Nucleic Acids Research* 22(10):1815–1820, 1994.
Nomura et al., "Isolation and Characterization of Retinoic Acid–Inducible cDNA Clones in F9 Cells: One of the Early Inducible Clones Encodes a Novel Protein Sharing Several Highly Homologous Regions with a *Drosophila polyhomeotic* Protein" *Differentiation* 57:39–50, 1994.

(List continued on next page.)

*Primary Examiner*—Paula K. Hutzell
*Assistant Examiner*—Anne L. Holleran
*Attorney, Agent, or Firm*—Jane E. R. Potter; Kimberlin L. Morley; Robert P. Blackburn

[57] ABSTRACT

Mammalian deep orange tumor suppressor genes are disclosed. Mammalian deep orange genes and proteins can be used as therapeutics, as diagnostic tools, and in making animal models. The genes can be used to identify a q13 region of a human chromosome 15 and a central region of a mouse chromosome 2.

15 Claims, 1 Drawing Sheet

OTHER PUBLICATIONS

Watson et al., "Drosophila in Cancer Research: the First Fifty Tumor Suppressor Genes" *J. Cell Science 18:*19–33, 1994.

Kanno et al., "mel–18, a Polycomb Group–Related Mammalian Gene, Encodes a Transcriptional Negative Regulator With Tumor Suppressive Activity" *The EMBO Journal 14*(22):5672–5678, 1995.

Santamaria and Randsholt, "Characterization of a Region of the X Chromosome of Drosophila Including multi sex combs (mxc), a Polycomb Group Gene which also Functions as a Tumour Suppressor" *Mol. Gen. Genet. 246:*282–290, 1995.

Pirrotta, "Chromatin Complexes Regulating Gene Expression in Drosophila" *Current Opinion in Genetics and Development 5:*466–472, 1995.

Stuart et al., "PAX and HOX in Neoplasia" *Advances in Genetics 33:*255–274, 1995.

Tamkun, "The Role of *Brahma* and Related Proteins in Transcription and Development" *Current Opinion in Genetics and Development 5:*473–477, 1995.

Yu et al., "Altered Hox Expression and Segmental Identity in MII–mutant Mice" *Nature 378:*505–508, Nov., 1995.

Database EMBL, entry MM37135, Accession No. W83371 (XP002047119) Jun. 1996.

Database EMBL, entry HS151A12F, Accession No. Z59350 (XP002047120) Oct. 1995.

Database EMBL, entry HS157201, Accession No. H51157 (XP0020447121) Sep. 1995.

Database EMBL, entry DMDORGE, Accession No. X86683 (XP002047147) May 1995.

Database EMBL, entry MMAA50122, Accession No. AA050122 (XP002047122) Nov. 1996.

Database EMBL, entry MMAA11260, Accession No. AA111260 (XP00047123) Nov. 1996.

Database EMBL, entry MMA71860, Accession No. AA071860 (XP002047124) Oct. 1996.

Database EMBL, entry MMA15039, Accession No. AA015039 (XP002047125) Aug. 1996.

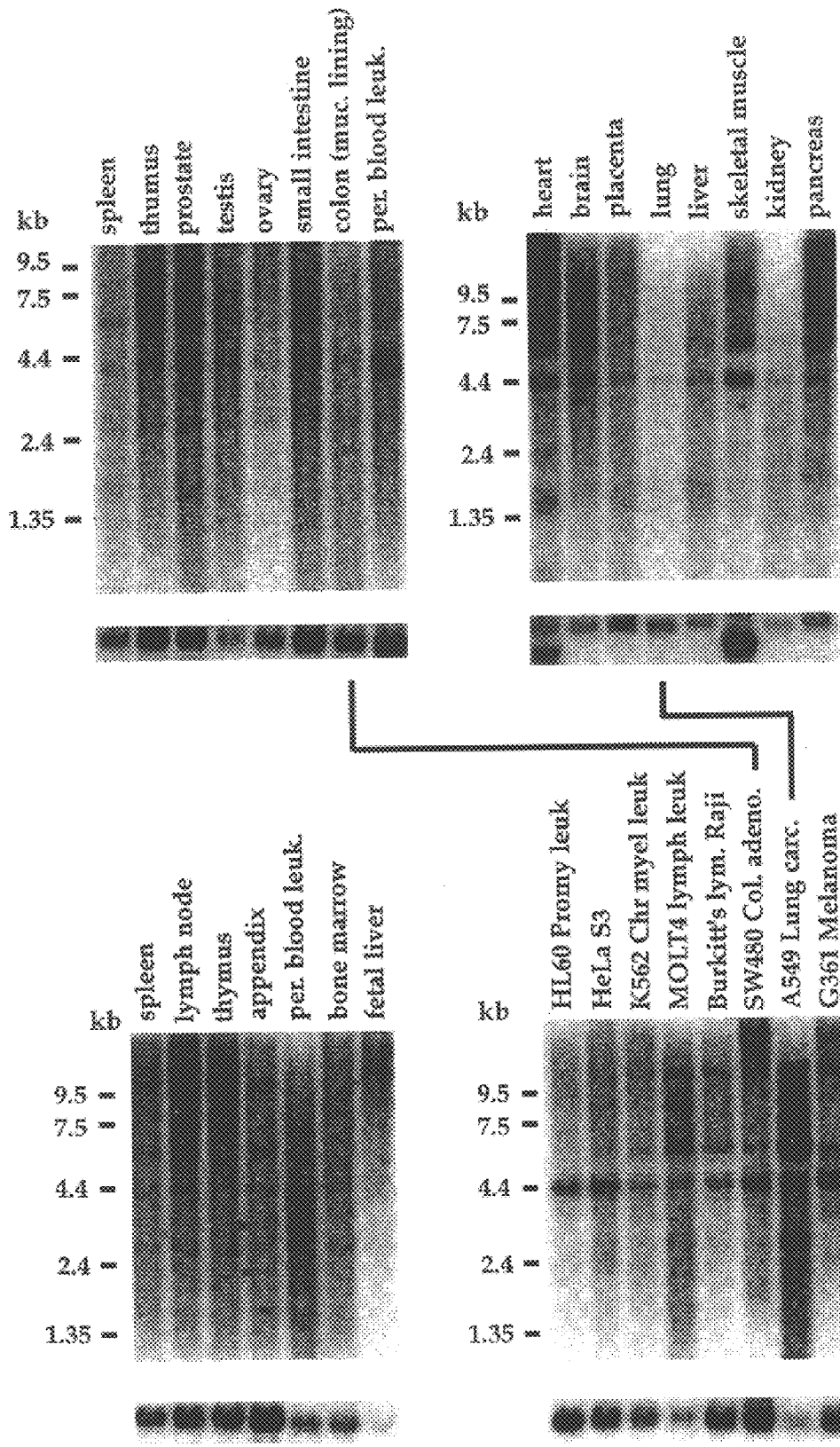

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1995 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
AGGCCACACT GCTGACCACC TGGCTGACAG AGCTCTACCT GAGCCGGCTT GGGGCTCTGC      60

AGGGCGACCC AGAGGCCCTG ACTCTCTACC GAGAAACCAA GGAATGCTTT CGAACCTTCC     120

TCAGCAGCCC CCGCCACAAA GAGTGGCTCT TTGCCAGCCG GGCCTCTATC CATGAGCTGC     180

TCGCCAGTCA TGGGGACACA GAACACATGG TGTACTTTGC AGTGATCATG CAGGACTATG     240

AGCGGGTGGT GGCTTACCAC TGTCAGCACG AGGCCTACGA GGAGGCCCTG GCCGTGCTCG     300

CCCGCCACCG TGACCCCCAG CTCTTCTACA AGTTCTCACC CATCCTCATC CGTCACATCC     360

CCCGCCAGCT TGTAGATGCC TGGATTGAGA TGGGCAGCCG GCTGGATGCT CGTCAGCTCA     420

TTCCTGCCCT GGTGAACTAC AGCCAGGGTG GTGAGGTCCA GCAGGTGAGC CAGGCCATCC     480

GCTACATGGA GTTCTGCGTG AACGTGCTGG GGGAGACTGA GCAGGCCATC CACAACTACC     540

TGCTGTCACT GTATGCCCGT GGCCGGCCGG ACTCACTACT GGCCTATCTG GAGCAGGCTG     600

GGGCCAGCCC CCACCGGGTG CATTACGACC TCAAGTATGC GCTGCGGCTC TGCGCCGAGC     660

ATGGCCACCA CCGCGCTTGT GTCCATGTCT ACAAGGTCCT AGAGCTGTAT GAGGAGGCCG     720

TGGACCTGGC CCTGCAGGTG GATGTGGACC TGGCCAAGCA GTGTGCAGAC CTGCCTGAGG     780

AGGATGAGGA ATTGCGCAAG AAGCTGTGGC TGAAGATCGC ACGGCACGTG GTGCAGGAAG     840

AGGAAGATGT ACAGACAGCC ATGGCTTGCC TGGCTAGCTG CCCCTTGCTC AAGATTGAGG     900

ATGTGCTGCC CTTCTTTCCT GATTTCGTCA CCATCGACCA CTTCAAGGAG GCGATCTGCA     960

GCTCACTTAA GGCCTACAAC CACCACATCC AGGAGCTGCA GCGGGAGATG GAAGAGGCTA    1020

CAGCCAGTGC CCAGCGCATC CGGCGAGACC TGCAGGAGCT GCGGGGCCGC TACGGCACTG    1080

TGGAGCCCCA GGACAAATGT GCCACCTGCG ACTTCCCCCT GCTCAACCGC CCTTTTTACC    1140

TCTTCCTCTG TGGCCATATG TTCCATGCTG ACTGCCTGCT GCAGGCTGTG CGACCTGGCC    1200
```

-continued

```
TGCCAGCCTA CAAGCAGGCC CGGCTGGAGG AGCTGCAGAG GAAGCTGGGG GCTGCTCCAC      1260

CCCCAGCCAA GGGCTCTGCC CGGGCCAAGG AGGCCGAGGG TGGGGCTGCC ACGGCAGGGC      1320

CCAGCCGGGA ACAGCTCAAG GCTGACCTGG ATGAGTTGGT GGCCGCTGAG TGTGTGTACT      1380

GTGGGGAGCT GATGATCCGC TCTATCGACC GGCCGTTCAT CGACCCCCAG CGCTACGAGG      1440

AGGAGCAGCT CAGTTGGCTG TAGGAGGGTG TCACCTTTGA TGGGGATGG GCAATGGGGA       1500

GCAGTGGCTT GAACCCACTT GAGAAGGCTG CCTCCTAGGC TCTGCTCAGT CATCTTGCAA      1560

TTGCCACACT GTGACCACGT TGACGGGAGT AGAGTAGCGC TGTTGGCCAG GAGGTGTCAG      1620

GTGTGAGTGT ATTCTGCCAG CTTTTCATGC TGTTCTTCAG AGCTGCAGTT ATGCCAGACC      1680

ATCAGCCTGC CTCCCAGTAG AGGCCCTTCA CCTGGAGAAG TCAGAAATCT GACCCAATTC      1740

CACCCCCTGC CTCTAGCACC TCTTCTGTCC CTGTCATTCC CCACACACGT CCTGTTCACC      1800

TCGAGAGAGA GAGAGAGAGA GCACCTTTCT TCCGTCTGTT CACTCTGCGG CCTCTGGAAT      1860

CCCAGCTCTT CTCTCTCAGA AGAAGCCTTC TCTTCCTCCT GCCTGTAGGT GTCCCAGAAG      1920

TGAGAAGGCA GCCTTCGAAG TCCTGGGCAT TGGGTGAGAA AGTGATGCTA GTTGGGGCAT      1980

GCTTTTGTGC ACACG                                                        1995
```

(2) INFORMATION FOR SEQ ID NO:2:

(i) SEQUENCE CHARACTERISTICS:
        (A) LENGTH: 486 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Ala Thr Leu Leu Thr Thr Trp Leu Thr Glu Leu Tyr Leu Ser Arg Leu
 1               5                  10                  15

Gly Ala Leu Gln Gly Asp Pro Glu Ala Leu Thr Leu Tyr Arg Glu Thr
            20                  25                  30

Lys Glu Cys Phe Arg Thr Phe Leu Ser Ser Pro Arg His Lys Glu Trp
        35                  40                  45

Leu Phe Ala Ser Arg Ala Ser Ile His Glu Leu Leu Ala Ser His Gly
    50                  55                  60

Asp Thr Glu His Met Val Tyr Phe Ala Val Ile Met Gln Asp Tyr Glu
65                  70                  75                  80

Arg Val Val Ala Tyr His Cys Gln His Glu Ala Tyr Glu Glu Ala Leu
                85                  90                  95

Ala Val Leu Ala Arg His Arg Asp Pro Gln Leu Phe Tyr Lys Phe Ser
            100                 105                 110

Pro Ile Leu Ile Arg His Ile Pro Arg Gln Leu Val Asp Ala Trp Ile
        115                 120                 125

Glu Met Gly Ser Arg Leu Asp Ala Arg Gln Leu Ile Pro Ala Leu Val
    130                 135                 140

Asn Tyr Ser Gln Gly Gly Glu Val Gln Gln Ser Gln Ala Ile Arg
145                 150                 155                 160

Tyr Met Glu Phe Cys Val Asn Val Leu Gly Glu Thr Glu Gln Ala Ile
                165                 170                 175

His Asn Tyr Leu Leu Ser Leu Tyr Ala Arg Gly Arg Pro Asp Ser Leu
            180                 185                 190

Leu Ala Tyr Leu Glu Gln Ala Gly Ala Ser Pro His Arg Val His Tyr
        195                 200                 205
```

```
Asp Leu Lys Tyr Ala Leu Arg Leu Cys Ala Glu His Gly His His Arg
    210                 215                 220
Ala Cys Val His Val Tyr Lys Val Leu Glu Leu Tyr Glu Ala Val
225                 230                 235                 240
Asp Leu Ala Leu Gln Val Asp Val Asp Leu Ala Lys Gln Cys Ala Asp
                245                 250                 255
Leu Pro Glu Glu Asp Glu Leu Arg Lys Lys Leu Trp Leu Lys Ile
                260                 265                 270
Ala Arg His Val Val Gln Glu Glu Asp Val Gln Thr Ala Met Ala
            275                 280                 285
Cys Leu Ala Ser Cys Pro Leu Leu Lys Ile Glu Asp Val Leu Pro Phe
290                 295                 300
Phe Pro Asp Phe Val Thr Ile Asp His Phe Lys Glu Ala Ile Cys Ser
305                 310                 315                 320
Ser Leu Lys Ala Tyr Asn His His Ile Gln Glu Leu Gln Arg Glu Met
                325                 330                 335
Glu Glu Ala Thr Ala Ser Ala Gln Arg Ile Arg Arg Asp Leu Gln Glu
            340                 345                 350
Leu Arg Gly Arg Tyr Gly Thr Val Glu Pro Gln Asp Lys Cys Ala Thr
            355                 360                 365
Cys Asp Phe Pro Leu Leu Asn Arg Pro Phe Tyr Leu Phe Leu Cys Gly
370                 375                 380
His Met Phe His Ala Asp Cys Leu Leu Gln Ala Val Arg Pro Gly Leu
385                 390                 395                 400
Pro Ala Tyr Lys Gln Ala Arg Leu Glu Glu Leu Gln Arg Lys Leu Gly
                405                 410                 415
Ala Ala Pro Pro Ala Lys Gly Ser Ala Arg Ala Lys Glu Ala Glu
            420                 425                 430
Gly Gly Ala Ala Thr Ala Gly Pro Ser Arg Glu Gln Leu Lys Ala Asp
            435                 440                 445
Leu Asp Glu Leu Val Ala Ala Glu Cys Val Tyr Cys Gly Glu Leu Met
    450                 455                 460
Ile Arg Ser Ile Asp Arg Pro Phe Ile Asp Pro Gln Arg Tyr Glu Glu
465                 470                 475                 480
Glu Gln Leu Ser Trp Leu
                485
```

(2) INFORMATION FOR SEQ ID NO:3:

(i) SEQUENCE CHARACTERISTICS:
    (A) LENGTH: 4602 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:3:

```
GGCACGAGCC GAAGTTTCCC TCAGGATAGC TGGCGCTCTC GCTCTTTTTT TCCCCGACGT      60

ACGCAGTTTT ATCCGGTAAA GCGAATGATT AGAGGTCTTG GGGCCGAAAC GATCTCAACC     120

TATTCTCAAA CTTTAAATGG GTAAGAAGCC CGGCTCGCTG GCGTGGAGCC GGGCGTGGAA     180

TGCGAGTGCC TAGTGGGCCA CTTTTGGTAA GCAGAACTGG CGCTGCGGGA TGAACCGAAC     240

GCCGGGTTAA GGCGCCCGAT GCCGACGCTC ATCACACCCC AGAAAGGTG TTGGTTGATA      300

TAGACAGCAG GACGGTGGCC ATGGAAGTCG GAATCCGCTA AGGAGTGTGT AACAACTCAC     360
```

-continued

```
CTGCCGAATC AACTAGCCCT GAAAATGGAT GGCGCTGGAG CGTCGGGCCC ATACCCGGCC      420

GTCGCCGGCA GTCGGAACGG GACGGGAGCG GCCGCGGGTG CGCGTCTCTC GGGGTCGGGG      480

GTGCGTGGCG GGGGCCCGTC CCCCGCCTCC CCTCCGCGCG CCGGGTTTCG CCCCCGCGGC      540

GTCGGGCCCC GCGGACGCTA CGCCGCGACG AGTAGGAGGG CCGCTGCGGT GAGCCTTGAA      600

GCCTAGGGCG CGGGCCCGGG TGGAGCCGCC GCAGGTGCAG ATCTTGGTGG TAGTAGCAAA      660

TATTCAAACG AGAACTTTGA AGGCCGAAGT GGAGAAGGGT TCCATGTGAA CAGCAGTTGA      720

ACATGGGACT GGAGCTGGGG TGCAAAGCTG CGCCATGGTC TAGTTGGGGC TCCTCGATCG      780

TCTCCTTCAC AGAGAAAGCG AAAAGGGCCT CAGAATTTTT AAAAGGTTCT CAGGATCTGT      840

CAGACGCTGG GGAAGCACAA CTTGCAAATC CAGGACGACC GGGGTCCCAG TTGTGACCCC      900

CAGCCCCCAG ATCAGAGATC CAGAACTTGA TTGCCATGGC GTCCATCCTG GATGAGTACG      960

AGGACTCATT GTCCCGCTCG GCCGTCTTGC AGACTGGTTG CCCTAGCGTG GGCATCCCCC     1020

ATTCTGGGTA TGTAAGTGCC CACCTGGAGA AGGAGGTGCC CATCTTCACC AAGCAGCGGG     1080

TTGACTTCAC CCCCTCGGAG CGGATCACTA GCCTCGTGGT CTCCTGCAAT CAGCTCTGCA     1140

TGAGCCTGGG CAAGGATACA CTGCTCCGCA TTGACTTGGG CAAGGCAAGT GAGCCCAACC     1200

GTGTGGAACT GGGGCGCAAG GACGACGCCA AAGTCCACAA GATGTTCCTG GACCATACTG     1260

GCTCTCATCT GCTGGTTGCG CTGAGTAGCA CCGAGGTCCT TTACATGAAC CGCAATGGAC     1320

AGAAGGCCCG GCCCCTGGCT CGCTGGAAGG GACAGCTGGT GGAGAGTGTG GGATGGAACA     1380

AGGCCATGGG CAACGAGAGC AGCACCGGCC CCATCCTGGT CGGCACAGCT CAAGGACAGA     1440

TCTTTGAAGC AGAGCTCTCA GCTAGCGAGG GTGGCCTCTT TGGCCCTGCC CCAGATCTCT     1500

ACTTCCGTCC ACTGTATGTG TTAAATGAAG AAGGGGGTCC AGCCCCTGTG TGCTCCCTCG     1560

AGGCTGAGCG TGGCCCCGAT GGCCGAGGCT TTGTCATTGC CACCACTCGG CAGCGCCTCT     1620

TCCAGTTCAT AGGCCGAGCT GTGGAAGATA CTGAAGCCCA GGGCTTCGCA GGACTCTTTG     1680

CTGCCTATAC AGACCACCCG CCCCCATTCC GTGAGTTTCC TAGCAACTTG GGGTATAGTG     1740

AGTTGGCTTT CTATACCCCT AAGTTACGCT CGGCACCTCG CGCCTTTGCC TGGATGATGG     1800

GAGATGGAGT GCTGTATGGC TCACTGGACT GCGGGCGTCC TGACTCGCTG CTGAGTGAGG     1860

AGCGAGTGTG GGAATACCCA GCGGGGGTTG GTCCTGGGGC CAATCCACCC TTAGCCATCG     1920

TCCTGACCCA GTTCCATTTC CTACTGCTGC TGGCCGACCG GGTGGAGGCT GTGTGCACGC     1980

TAACAGGGCA GGTGGTGCTA CGGGATCACT TCCTGGAGAA GTTTGGACCA CTGAGGCACA     2040

TGGTGAAGGA CTCATCCACA GGCCACCTAT GGGCCTACAC TGAGCGTGCG GTCTTCCGCT     2100

ACCATGTGCA ACGTGAGGCA CGGGATGTCT GGCGCACCTA CTTGGACATG AACCGCTTTG     2160

ACCTGGCCAA AGAGTATTGT AGAGAGCGGC CTGATTGCCT GGACACGGTC CTGGCCCGAG     2220

AGGCTGATTT CTGTTTTCGC CAGCATCGCT ACCTGGAGAG CGCCCGCTGC TATGCGCTGA     2280

CACAGAGCTA TTTTGAGGAG ATTGCCCTCA AGTTCTTGGA GGCCCGGCAA GAGGAGGCGC     2340

TGGCCGAGTT TCTCCAGCGG AAACTGGCCG GCTTGAAGCC GACGGAGCGT ACCCAGGCCA     2400

CACTGCTGAC CACTTGGCTG ACAGAGCTCT ACCTGAGCCG CCTGGGTGCT CTGCAGGGTG     2460

ACCCAGATGC TCTGACTCTC TACCGGGACA CACGGGAGTG TTTCCGTACT TTTCTCAGTA     2520

GCCCTCGGCA CAAAGAGTGG CTCTTTGCTA GCCGGGCCTC TATCCACGAG CTGCTCGCCA     2580

GTCACGGAGA CACAGAGCAC ATGGTTTATT TTGCAGTGAT CATGCAGGAC TATGAACGGG     2640

TGGTCGCATA CCACTGTCAG CATGAGGCTT ACGAGGAGGC CCTGGCTGTG CTTGCCCGCC     2700
```

-continued

```
ACCGGGACCC CCAGCTCTTC TACAAATTCT CCCCCATTCT CATCCGCCAC ATCCCCCGCC      2760

AGCTCGTAGA CGCCTGGATT GAGATGGGCA GCCGGCTGGA TGCTCGGCAG CTCATCCCTG      2820

CCCTGGTGAA CTACAGCCAG GGCGGTGAGG CCCAGCAGGT GAGCCAGGCC ATCCGCTACA      2880

TGGAATTCTG CGTGAATGTG CTCGGTGAGA CGGAGCAGGC CATTCACAAC TACCTGCTGT      2940

CCCTGTATGC CCGTGGCCAG CCAGCCTCAC TTCTGGCATA CCTGGAACAA GCTGGGGCCA      3000

GCCCGCACCG TGTACATTAT GATCTCAAAT ATGCACTTCG ACTTTGTGCT GAGCACGGCC      3060

ACCACCGCGC CTGCGTCCAT GTCTATAAGG TGTTGGAGCT ATATGAGGAG CTGTGGACC       3120

TGGCCCTGCA GGTGGATGTG GACCTGGCCA AGCAGTGTGC AGACTTGCCG GAGGAGGATG     3180

AGGAACTTCG CAAGAAACTA TGGCTCAAGA TCGCCCGGCA CGTGGTGCAG GAGGAAGAAG     3240

ACGTCCAGAC AGCCATGGCC TGCTTGGCCA GCTGCCCCTT GCTCAAGATC GAGGATGTGC     3300

TACCCTTCTT CCCTGACTTT GTCACCATCG ACCACTTCAA GGAGGCAATC TGTAGTTCCC     3360

TGAAGGCCTA CAACCACCAC ATCCAGGAGC TGCAGCGCGA GATGGAAGAA GCCACAGCCA     3420

GTGCCCAGCG CATCCGACGA GACTTGCAGG AGCTCCGAGG CCGCTATGGC ACCGTGGAGC     3480

CCCAGGACAA ATGCTCCACC TGTGACTTTC CTTTGCTCAT CCGACCCTTT TACCTGTTTC     3540

TCTGTGGCCA CATGTTTCAC GCTGACTGTC TCCTACAGGC TGTGCGGCCC GGCCTCCCTG     3600

CCTACAAGCA GGCCAGACTT GAGGAACTGC ACCGCAAGCT TGGGGCGGCG CCTCCTCCGA     3660

CCAAAGGCTC CGTGAAGGCC AAGGAGGCAG AAGCTGGGGC TGCAGCGGTG GGGCCCAGCC     3720

GGGAGCAGCT CAAGGCTGAC CTGGATGAGC TGGTGGCTGC TGAGTGTGTG TACTGTGGGG     3780

AGCTGATGAT TCGGTCTATC GACCGGCCCT TCATTGATCC GCAGCGCTAT GAGGAGGAGC     3840

ACCTCAGCTG GCTATAGGAA GTTCCCCCGC ATGGGTGGAC AGACATGGAT CCAGCTGCCA     3900

GACCCTCCTG CGAAAGCCAG GCCCTGGTTG GTGTTCGGTC CTTGAGCTTG CCGGGTCTGC     3960

GATTGTGAGG GGGTTGCAGC CAAGCTTCAG CCGGGAGGTT TTCAGGTGCG AACGCCGAGC     4020

TGTGCTTCAG ACCTGTCTTA GACCTGCCCG TCCCAGGCAA CCCGAGCTGG TGAGATCAGC     4080

CGTGATCCTT TTAACCACTA CATCTAACAG TTCCTCTGTT CTCGTTAGCA TGTTCACCTG     4140

GACTGAGTGG CCCGCTGTCC TTCCTTCCTC CGTCCTTCCA CAGCCTCTGG ACCTCCAGCT     4200

CGCCCTCTTC TGCCTCAACT AGGTGACCCA GGAGCAAGCA GGCAGACCCT AGGCACTTGT     4260

GGGGAGAGTG GGCATGTGGA GATGCTAATG TGACCTGGGG CTCCAGTGTC GGGTGCCCTG     4320

AGGCTGAGGG CACACCTGGG ACAAGGGGAA ATAGGGAGAG TATTAAATTG TGCTACAATG     4380

GTGGCCCTGG ACTTGATGGC TTTGTGTTGA TGCTGAAGCT AACAGGATAT GATCCCAAGA     4440

AAGGATGGAA TGCCACAAGA AGGCTGCCTG CACCAAGTGT GGAATAGAAC AGGTCAGGTC     4500

ACGGCCAGCC TAGTCGACAT AATAAGTTCT AGGCCAGCAA AGGCTACGTA GTATGACCCT     4560

GCCTGTCTCA AAAAAAAAA AATTAAATTA AATTAAAAAA AA                         4602
```

(2) INFORMATION FOR SEQ ID NO:4:

(i) SEQUENCE CHARACTERISTICS:
        (A) LENGTH: 973 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Ala Ser Ile Leu Asp Glu Tyr Glu Asp Ser Leu Ser Arg Ser Ala
1               5                   10                  15
```

-continued

```
Val Leu Gln Thr Gly Cys Pro Ser Val Gly Ile Pro His Ser Gly Tyr
                20                  25                  30

Val Ser Ala His Leu Glu Lys Glu Val Pro Ile Phe Thr Lys Gln Arg
                35                  40                  45

Val Asp Phe Thr Pro Ser Glu Arg Ile Thr Ser Leu Val Ser Cys
 50                  55                  60

Asn Gln Leu Cys Met Ser Leu Gly Lys Asp Thr Leu Leu Arg Ile Asp
 65                  70                  75                  80

Leu Gly Lys Ala Ser Glu Pro Asn Arg Val Glu Leu Gly Arg Lys Asp
                85                  90                  95

Asp Ala Lys Val His Lys Met Phe Leu Asp His Thr Gly Ser His Leu
                100                 105                 110

Leu Val Ala Leu Ser Ser Thr Glu Val Leu Tyr Met Asn Arg Asn Gly
                115                 120                 125

Gln Lys Ala Arg Pro Leu Ala Arg Trp Lys Gly Gln Leu Val Glu Ser
                130                 135                 140

Val Gly Trp Asn Lys Ala Met Gly Asn Glu Ser Ser Thr Gly Pro Ile
145                 150                 155                 160

Leu Val Gly Thr Ala Gln Gly Gln Ile Phe Glu Ala Glu Leu Ser Ala
                165                 170                 175

Ser Glu Gly Gly Leu Phe Gly Pro Ala Pro Asp Leu Tyr Phe Arg Pro
                180                 185                 190

Leu Tyr Val Leu Asn Glu Glu Gly Pro Ala Pro Val Cys Ser Leu
                195                 200                 205

Glu Ala Glu Arg Gly Pro Asp Gly Arg Gly Phe Val Ile Ala Thr Thr
                210                 215                 220

Arg Gln Arg Leu Phe Gln Phe Ile Gly Arg Ala Val Glu Asp Thr Glu
225                 230                 235                 240

Ala Gln Gly Phe Ala Gly Leu Phe Ala Ala Tyr Thr Asp His Pro Pro
                245                 250                 255

Pro Phe Arg Glu Phe Pro Ser Asn Leu Gly Tyr Ser Glu Leu Ala Phe
                260                 265                 270

Tyr Thr Pro Lys Leu Arg Ser Ala Pro Arg Ala Phe Ala Trp Met Met
                275                 280                 285

Gly Asp Gly Val Leu Tyr Gly Ser Leu Asp Cys Gly Arg Pro Asp Ser
                290                 295                 300

Leu Leu Ser Glu Glu Arg Val Trp Glu Tyr Pro Ala Gly Val Gly Pro
305                 310                 315                 320

Gly Ala Asn Pro Pro Leu Ala Ile Val Leu Thr Gln Phe His Phe Leu
                325                 330                 335

Leu Leu Leu Ala Asp Arg Val Glu Ala Val Cys Thr Leu Thr Gly Gln
                340                 345                 350

Val Val Leu Arg Asp His Phe Leu Glu Lys Phe Gly Pro Leu Arg His
                355                 360                 365

Met Val Lys Asp Ser Ser Thr Gly His Leu Trp Ala Tyr Thr Glu Arg
                370                 375                 380

Ala Val Phe Arg Tyr His Val Gln Arg Glu Ala Arg Asp Val Trp Arg
385                 390                 395                 400

Thr Tyr Leu Asp Met Asn Arg Phe Asp Leu Ala Lys Glu Tyr Cys Arg
                405                 410                 415

Glu Arg Pro Asp Cys Leu Asp Thr Val Leu Ala Arg Glu Ala Asp Phe
                420                 425                 430
```

-continued

```
Cys Phe Arg Gln His Arg Tyr Leu Glu Ser Ala Arg Cys Tyr Ala Leu
            435                 440                 445

Thr Gln Ser Tyr Phe Glu Glu Ile Ala Leu Lys Phe Leu Glu Ala Arg
        450                 455                 460

Gln Glu Glu Ala Leu Ala Glu Phe Leu Gln Arg Lys Leu Ala Gly Leu
465                 470                 475                 480

Lys Pro Thr Glu Arg Thr Gln Ala Thr Leu Leu Thr Thr Trp Leu Thr
                485                 490                 495

Glu Leu Tyr Leu Ser Arg Leu Gly Ala Leu Gln Gly Asp Pro Asp Ala
            500                 505                 510

Leu Thr Leu Tyr Arg Asp Thr Arg Glu Cys Phe Arg Thr Phe Leu Ser
            515                 520                 525

Ser Pro Arg His Lys Glu Trp Leu Phe Ala Ser Arg Ala Ser Ile His
        530                 535                 540

Glu Leu Leu Ala Ser His Gly Asp Thr Glu His Met Val Tyr Phe Ala
545                 550                 555                 560

Val Ile Met Gln Asp Tyr Glu Arg Val Val Ala Tyr His Cys Gln His
                565                 570                 575

Glu Ala Tyr Glu Glu Ala Leu Ala Val Leu Ala Arg His Arg Asp Pro
            580                 585                 590

Gln Leu Phe Tyr Lys Phe Ser Pro Ile Leu Ile Arg His Ile Pro Arg
        595                 600                 605

Gln Leu Val Asp Ala Trp Ile Glu Met Gly Ser Arg Leu Asp Ala Arg
610                 615                 620

Gln Leu Ile Pro Ala Leu Val Asn Tyr Ser Gln Gly Gly Glu Ala Gln
625                 630                 635                 640

Gln Val Ser Gln Ala Ile Arg Tyr Met Glu Phe Cys Val Asn Val Leu
                645                 650                 655

Gly Glu Thr Glu Gln Ala Ile His Asn Tyr Leu Leu Ser Leu Tyr Ala
            660                 665                 670

Arg Gly Gln Pro Ala Ser Leu Leu Ala Tyr Leu Glu Gln Ala Gly Ala
        675                 680                 685

Ser Pro His Arg Val His Tyr Asp Leu Lys Tyr Ala Leu Arg Leu Cys
690                 695                 700

Ala Glu His Gly His His Arg Ala Cys Val His Val Tyr Lys Val Leu
705                 710                 715                 720

Glu Leu Tyr Glu Glu Ala Val Asp Leu Ala Leu Gln Val Asp Val Asp
                725                 730                 735

Leu Ala Lys Gln Cys Ala Asp Leu Pro Glu Glu Asp Glu Leu Arg
            740                 745                 750

Lys Lys Leu Trp Leu Lys Ile Ala Arg His Val Val Gln Glu Glu
        755                 760                 765

Asp Val Gln Thr Ala Met Ala Cys Leu Ala Ser Cys Pro Leu Leu Lys
770                 775                 780

Ile Glu Asp Val Leu Pro Phe Phe Pro Asp Phe Val Thr Ile Asp His
785                 790                 795                 800

Phe Lys Glu Ala Ile Cys Ser Ser Leu Lys Ala Tyr Asn His His Ile
                805                 810                 815

Gln Glu Leu Gln Arg Glu Met Glu Glu Ala Thr Ala Ser Ala Gln Arg
            820                 825                 830

Ile Arg Arg Asp Leu Gln Glu Leu Arg Gly Arg Tyr Gly Thr Val Glu
        835                 840                 845

Pro Gln Asp Lys Cys Ser Thr Cys Asp Phe Pro Leu Leu Ile Arg Pro
```

-continued

```
                      850                 855                 860
Phe Tyr Leu Phe Leu Cys Gly His Met Phe His Ala Asp Cys Leu Leu
865                 870                 875                 880

Gln Ala Val Arg Pro Gly Leu Pro Ala Tyr Lys Gln Ala Arg Leu Glu
                885                 890                 895

Glu Leu His Arg Lys Leu Gly Ala Ala Pro Pro Pro Thr Lys Gly Ser
            900                 905                 910

Val Lys Ala Lys Glu Ala Glu Ala Gly Ala Ala Ala Val Gly Pro Ser
        915                 920                 925

Arg Glu Gln Leu Lys Ala Asp Leu Asp Glu Leu Val Ala Ala Glu Cys
    930                 935                 940

Val Tyr Cys Gly Glu Leu Met Ile Arg Ser Ile Asp Arg Pro Phe Ile
945                 950                 955                 960

Asp Pro Gln Arg Tyr Glu Glu Glu His Leu Ser Trp Leu
                965                 970
```

MAMMALIAN DEEP ORANGE NUCLEOTIDES

This application claims the benefit of the following copending provisional applications: Ser. No.60/022,988, filed Aug. 2, 1996, Ser. No.60/030,337, filed Nov. 5, 1996, and Ser. No. 60/045,886, filed Apr. 30, 1997, each of which is incorporated by reference herein.

TECHNICAL AREA OF THE INVENTION

The invention relates to the area of tumor suppression. More particularly, the invention relates to tumor suppressor genes and proteins.

BACKGROUND OF THE INVENTION

Mutations in tumor suppressor genes play an important role in the development of neoplasias. Manipulation of tumor suppressor gene expression can be used to prevent or treat neoplasias. Detection of mutations in tumor suppressor genes can also be used to detect neoplastic cells and genetic predispositions to neoplasias. Thus, there is a need in the art for the identification of mammalian tumor suppressor genes which can be used to develop methods of diagnosing, prognosing, and treating neoplastic cells in humans and other mammals.

SUMMARY OF THE INVENTION

It is an object of the invention to provide an isolated and purified deep orange protein.

It is another object of the invention to provide an isolated and purified deep orange polypeptide.

It is yet another object of the invention to provide a deep orange fusion protein.

It is still another object of the invention to provide a preparation of antibodies which specifically bind to a deep orange protein.

It is yet another object of the invention to provide an isolated and purified subgenomic polynucleotide.

It is still another object of the invention to provide an expression construct for expressing all or a portion of a deep orange protein.

It is even another object of the invention to provide a mammal which does not express an endogenous wild-type deep orange gene in one or more tissues.

It is another object of the invention to provide a method to aid in the diagnosis or prognosis of cancer in a mammal.

It is yet another object of the invention to provide a method to aid in detecting a genetic predisposition to neoplasia in a mammal.

It is still another object of the invention to provide a method of identifying a human chromosome 15.

It is even another object of the invention to provide a method of identifying a mouse chromosome 2.

These and other objects of the invention are provided by one or more of the embodiments described below.

One embodiment of the invention provides an isolated and purified deep orange protein. The deep orange protein has an amino acid sequence which is at least 95% identical to the amino acid sequence shown in SEQ ID NO:4.

Another embodiment of the invention provides an isolated and purified deep orange polypeptide. The deep orange polypeptide comprises at least eight contiguous amino acids. The amino acid sequence of the at least eight contiguous amino acids is at least 95% identical to the amino acid sequence shown in SEQ ID NO:4.

Yet another embodiment of the invention provides a deep orange fusion protein. The fusion protein comprises a first protein segment and a second protein segment fused together by means of a peptide bond. The first protein segment consists of at least eight contiguous amino acids of a deep orange protein. The amino acid sequence of the deep orange protein is at least 95% identical to the amino acid sequence shown in SEQ ID NO:4.

Still another embodiment of the invention provides a preparation of antibodies which specifically bind to a deep orange protein. The amino acid sequence of the deep orange protein is at least 95% identical to the amino acid sequence shown in SEQ ID NO:4.

Even another embodiment of the invention provides an isolated and purified subgenomic polynucleotide. The polynucleotide comprises at least 1340 contiguous nucleotides and encodes an amino acid sequence which is at least 95% identical to the amino acid sequence shown in SEQ ID NO:4.

Yet another embodiment of the invention provides an expression construct for expressing all or a portion of a deep orange protein. The expression construct comprises a promoter and a polynucleotide segment. The promoter is not one which initiates transcription of a deep orange gene in normal human cells. The polynucleotide segment is located downstream from the promoter and encodes at least eight contiguous amino acids of a deep orange protein. The deep orange protein has at least 95% identity with the amino acid sequence shown in SEQ ID NO:4. Transcription of the polynucleotide segment initiates at the promoter.

Still another embodiment of the invention provides a mammal which does not express an endogenous wild-type deep orange gene in one or more tissues. The tissues are selected from the group consisting of: spleen, thymus, prostate, testis, ovary, small intestine, mucosal lining of the colon, heart, brain, placenta, liver, skeletal muscle, pancreas, lymph node, appendix, peripheral blood leukocytes, and bone marrow.

Even another embodiment of the invention provides a method to aid in the diagnosis or prognosis of cancer in a mammal. The method comprises comparing a deep orange gene, mRNA, or protein in a first tissue of a mammal suspected of being neoplastic with a deep orange gene, mRNA, or protein in a second tissue of the mammal which is normal. A difference between the deep orange gene, mRNA, or protein in the first and second tissues indicates a mutation in the deep orange gene in the first tissue of the mammal.

Another embodiment of the invention provides a method to aid in detecting a genetic predisposition to neoplasia in a mammal. The method comprises comparing a deep orange gene, mRNA, or protein in a fetal tissue of a mammal with a wild-type deep orange gene, mRNA, or protein. A difference between the deep orange gene, mRNA, or protein in the fetal tissue of the mammal and the wild-type deep orange gene, mRNA, or protein indicates a genetic predisposition to neoplasia in the mammal.

Yet another embodiment of the invention provides a method of identifying a human chromosome 15. The method comprises the steps of contacting a preparation of metaphase human chromosomes with a nucleotide probe and detecting a chromosome which specifically hybridizes to the nucleotide probe. The probe comprises at least 12 contiguous nucleotides selected from the nucleotide sequence shown in SEQ ID NO:1. A chromosome which specifically hybridizes to the nucleotide probe is identified as a human chromosome 15.

Even another embodiment of the invention provides a method of identifying a mouse chromosome 2. The method comprises the steps of contacting a preparation of metaphase mouse chromosomes with a nucleotide probe and detecting a chromosome which specifically hybridizes to the nucleotide probe. The probe comprises at least 12 contiguous nucleotides selected from the nucleotide sequence shown in SEQ ID NO:3. A chromosome which specifically hybridizes to the nucleotide probe is identified as a mouse chromosome 2.

The present invention thus provides the art with novel mammalian tumor suppressor genes called "deep orange." Mammalian deep orange genes and proteins can be used, inter alia, in methods to aid in diagnosing and prognosing neoplasia, to detect predispositions to neoplasia, to create animal models which can be used to develop therapeutic treatments for neoplasia, and to identify a q13 region of a human chromosome 15 and a central region of a mouse chromosome 2.

BRIEF DESCRIPTION OF THE DRAWINGS

FIG. 1. Northern blots probed with a human deep orange nucleotide probe. The FIGURE depicts deep orange mRNA expression in human tissues and cancer cell lines.

DETAILED DESCRIPTION OF THE PREFERRED EMBODIMENTS

It is a discovery of the present invention that mammalian deep orange genes function as tumor suppressors. The deep orange genes can be used as diagnostic tools, to make animal models which can be used to develop therapeutic treatments for neoplasia, and to identify human chromosome 15 and mouse chromosome 2.

Mouse deep orange protein has the amino acid sequence shown in SEQ ID NO:4. While not wanting to be bound by any particular theory, it is believed that there are lethal alleles of deep orange which are involved in neoplasias, such as melanoma. In addition, it is believed that deep orange is involved in vacuolar or vesicle sorting.

The mouse deep orange gene maps to the central region of mouse chromosome 2, at or near the mouse pallid (pa) locus. Pallid mutants are a model for genetic emphysema. DeSanti et al., *Laboratory Investigation* 73, 40 (1995). Pallid mutants also have, inter alia, pigmentation defects, defects in vesicle sorting, elevated kidney lysosomal enzymes, and a deficiency in platelet dense granules, resulting in a platelet storage pool deficiency. Thus, these phenotypes may be the result of deep orange mutations.

A mammalian deep orange protein has an amino acid sequence which is at least 75, 80, 85, 90, 95, or 97% identical to the amino acid sequence of the mouse deep orange protein shown in SEQ ID NO:4. Preferably, the mammalian deep orange protein is a human deep orange protein. A human deep orange protein includes the amino acid sequence shown in SEQ ID NO:2. The sequence of amino acids shown in SEQ ID NO:2 is 97% identical to the C-terminal amino acids of the mouse deep orange protein shown in SEQ ID NO:4. Thus, the amino acid sequence of a human deep orange protein is overall at least 75, 80, 85, 90, 95, or 97% identical to the amino acid sequence shown in SEQ ID NO:4. The human deep orange gene maps to human chromosome 15q13.

Human deep orange mRNA comprises two major transcripts which measure 4.2 kb and 6 kb on Northern blots of human polyA+RNA probed with a human deep orange nucleotide probe (FIG. 1). The 4.2 and 6 kb transcripts are expressed, inter alia, in adult spleen, thymus, prostate, testis, ovary, small intestine, mucosal lining of the colon, heart, brain, placenta, liver, skeletal muscle, pancreas, lymph node, appendix, peripheral blood leukocytes, and bone marrow. The 4.2 kb and 6 kb deep orange transcripts are not detectable in lung, kidney, or fetal liver. A third deep orange transcript, measuring 11 kb on a Northern blot of human polyA+RNA (FIG. 1), is expressed in adult spleen, thymus, peripheral blood leukocytes, lymph node, bone marrow, skeletal muscle, heart, brain and pancreas. The 11 kb transcript is also expressed in cancer cell lines such as HL60 (promyelogenous leukemia), HeLa S3 (cervical carcinoma), K562 (chronic myelogenous leukemia), MOLT4 (lymphocytic leukemia), Burkitt's lymphoma Raji, SW480 (colon carcinoma), A549 (lung carcinoma), and G361 (melanoma).

Deep orange polypeptides comprise at least eight contiguous amino acids. The sequence of the amino acids in the deep orange polypeptide is at least 95% identical to the amino acid sequence shown in SEQ ID NO:4. A deep orange polypeptide can comprise at least eight contiguous amino acids of SEQ ID NO:4. In a preferred embodiment, the deep orange polypeptide comprises at least eight contiguous amino acids of SEQ ID NO:2.

Full-length mammalian deep orange proteins and polypeptides are useful for generating antibodies against mammalian amino acid sequences. Mammalian deep orange proteins and polypeptides can be isolated and purified from mammalian cells such as spleen, thymus, prostate, testis, ovary, small intestine, mucosal lining of the colon, heart, brain, placenta, liver, skeletal muscle, pancreas, lymph node, appendix, peripheral blood leukocytes, or bone marrow, by any method known in the art. These methods include, but are not limited to, size exclusion chromatography, ammonium sulfate fractionation, ion exchange chromatography, affinity chromatography, crystallization, electrofocusing and preparative gel electrophoresis. The skilled artisan can readily select methods which will result in a preparation of mammalian deep orange protein or polypeptide which is substantially free from other proteins and from carbohydrates, lipids, or subcellular organelles. A preparation of isolated and purified mammalian deep orange protein is at least 80% pure; preferably, the preparations are 90%, 95%, or 99% pure. Purity of the preparations may be assessed by any means known in the art, such as SDS-polyacrylamide gel electrophoresis.

Alternatively, mammalian deep orange proteins or polypeptides may be produced by recombinant DNA methods or by synthetic chemical methods. For production of recombinant mammalian deep orange proteins or polypeptides, mammalian deep orange coding sequences selected from the nucleotide sequences shown in SEQ ID NOS:1 or 3 can be expressed in known prokaryotic or eukaryotic expression systems. Bacterial, yeast, insect, or mammalian expression systems may be used, as is known in the art. Full-length mammalian deep orange cDNA, obtained by hybridizing human or mouse deep orange coding sequences with cDNA of a mammal can also be used to express mammalian deep orange proteins and polypeptides. Synthetic chemical methods, such as solid phase peptide synthesis, can be used to synthesize mammalian deep orange proteins or polypeptides.

Fusion proteins containing at least eight contiguous mammalian deep orange amino acid sequences can also be constructed. Mammalian deep orange fusion proteins are useful for generating antibodies against mammalian deep orange amino acid sequences and for use in various assay systems. For example, mammalian deep orange fusion proteins can be used to identify proteins which interact with deep orange protein and influence its function. Physical methods, such as protein affinity chromatography, or library-based assays for protein-protein interactions, such as the yeast two-hybrid or phage display systems, can be used for this purpose. Such methods are well known in the art.

A fusion protein comprises two protein segments fused together by means of a peptide bond. The first protein segment comprises at least 8, 10, 12, 15, or 20 contiguous amino acids of a mammalian deep orange protein. The amino acids may be selected from either SEQ ID NO:2 or SEQ ID NO:4 or from an amino acid sequence which is at least 75, 80, 85, 90, 95, or 97% identical to that shown in SEQ ID NO:4. The first protein segment can also be a full-length mammalian deep orange protein. The second protein segment can be a full-length protein or a protein fragment or polypeptide. The fusion protein can be labeled with a detectable marker, as is known in the art, such as a radioactive, fluorescent, chemiluminescent, or biotinylated marker. The second protein segment can be an enzyme which will generate a detectable product, such as β-galactosidase or other enzymes which are known in the art.

Techniques for making fusion proteins, either recombinantly or by covalently linking two protein segments, are also well known. Recombinant DNA methods can be used to construct deep orange fusion proteins, for example, by making a DNA construct which comprises mammalian deep orange coding sequences selected from SEQ ID NOS:1 or 3 in proper reading frame with nucleotides encoding the second protein segment and expressing the DNA construct in a host cell, as described below.

Isolated and purified mammalian deep orange proteins, polypeptides, or fusion proteins can be used as immunogens, to obtain a preparation of antibodies which specifically bind to a mammalian deep orange protein. The antibodies can be used to detect wild-type deep orange proteins in mammalian tissue. The antibodies can also be used to detect the presence of mutations in mammal deep orange genes which result in over- or under-expression of the deep orange protein or in deep orange proteins with altered size or electrophoretic mobilities.

Preparations of polyclonal and monoclonal mammalian deep orange antibodies can be made using standard methods known in the art. The antibodies specifically bind to epitopes present in mammalian deep orange proteins having amino acid sequences which are at least 75, 80, 85, 90, 95, or 97% identical to the amino acid sequence shown in SEQ ID NO:4. Preferably, the deep orange protein to which the antibodies specifically bind is a human deep orange protein comprising the amino acid sequence shown in SEQ ID NO:2. Preferably, the deep orange epitopes are not present in other mammal proteins. Typically, at least 6, 8, 10, or 12 contiguous amino acids are required to form an epitope. However, epitopes which involve non-contiguous amino acids may require more, e.g., at least 15, 25, or 50 amino acids. Antibodies which specifically bind to mammalian deep orange proteins provide a detection signal at least 5-, 10-, or 20-fold higher than a detection signal provided with other proteins when used in Western blots or other immunochemical assays. Preferably, antibodies which specifically bind mammalian deep orange proteins do not detect other proteins in immunochemical assays and can immunoprecipitate deep orange proteins from solution.

Mammalian deep orange antibodies can be purified by methods well known in the art. Preferably, the antibodies are affinity purified, by passing antiserum over a column to which a mammalian deep orange protein, polypeptide, or fusion protein is bound. The bound antibodies can then be eluted from the column, for example using a buffer with a high salt concentration.

Purified and isolate mammalian deep orange subgenomic polynucleotides can be used, inter alia, to obtain additional copies of the polynucleotides, to express deep orange proteins, polypeptides, or fusion proteins, and as probes for identifying wild-type and mutant deep orange coding sequences. The probes can also be used to identify a long arm of a human chromosome 15 and the central region of a mouse chromosome 2, as described below.

Purified and isolated mammalian deep orange subgenomic polynucleotides of the invention comprise at least 1340 contiguous nucleotides and encode an amino acid sequence which is at least 75, 80, 85, 90, 95, or 97% identical to the amino acid sequence shown in SEQ ID NO:4. In one embodiment, the polynucleotide comprises the nucleotide sequence shown in SEQ ID NO:3. In a preferred embodiment, the polynucleotide comprises the nucleotide sequence shown in SEQ ID NO:1. Subgenomic polynucleotides according to the invention contain less than a whole chromosome. Preferably, the polynucleotides are intron-free. Isolated polynuleotides are in preparations free or at least 90% free of other molecules.

Polynucleotides encoding a mammalian deep orange protein can be obtained by contacting cDNA of a mammal with a nucleotide probe of at least 10, 12, 14, 16, or 18 nucleotides of a mammal deep orange gene. Preferably, the cDNA is human cDNA. Mammalian deep orange polynucleotides can be isolated and purified free from other nucleotide sequences using standard nucleic acid purification techniques. For example, restriction enzymes and probes can be used to isolate polynucleotide fragments which comprise the deep orange coding sequences.

Complementary DNA encoding mammalian deep orange proteins can be made using reverse transcriptase, with deep orange mRNA as a template. The polymerase chain reaction (PCR) can be used to obtain the polynucleotides, using either genomic DNA or cDNA as a template. Alternatively, synthetic chemistry techniques can be used to synthesize the polynucleotide molecules of the invention. The degeneracy of the genetic code allows alternate nucleotide sequences to be synthesized which will encode a deep orange protein having an amino acid sequence which is at least 75, 80, 85, 90, 95, or 97% identical to the amino acid sequence shown in SEQ ID NO:4. All such nucleotide sequences are within the scope of the present invention.

A polynucleotide of the present invention can be used in an expression construct, to express all or a portion of a mammalian deep orange protein in a host cell. The host cell comprising the expression construct can be prokaryotic or eukaryotic. A variety of host cells for use in bacterial, yeast, insect and mammalian expression systems are available and can be used to express the expression construct. The expression constructs can be introduced into the host cells using any technique known in the art. These techniques include transferrin-polycation-mediated DNA transfer, transfection with naked or encapsulated nucleic acids, liposome-mediated cellular fusion, intracellular transportation of DNA-coated latex beads, protoplast fusion, viral infection, electroporation, and calcium phosphate-mediated transfection.

The expression construct comprises a promoter which is functional in the particular host cell selected, however the promoter is not the promoter which initiates transcription of the endogenous deep orange gene in human cells. The expression construct can also contain a trascription terminator which is functional in the host cell. The expression construct comprises a polynucleotide segment which encodes all or a portion of a deep orange protein. The polynucleotide segment is located downstream from the promoter. Transcription of the polynucleotide segment initiates at the promoter. The expression construct can be linear or circular and can contain sequences, if desired, for autonomous replication.

The human deep orange gene maps to human chromosome region 15q13. The mouse deep orange gene maps to the central region of the mouse chromosome 2. Thus, the subgenomic polynucleotides of the invention can be used to identify these chromosome regions in metaphase spreads of human or mouse chromosomes. Preparations of human or mouse metaphase chromosomes can be prepared using standard cytogenetic techniques from human or mouse primary tissues or cell lines.

Nucleotide probes comprising at least 12 contiguous nucleotides are used to identify the human or mouse chromosomes. For identification of the human chromosome region 15q13, the nucleotide probe comprises nucleotides selected from the nucleotide sequence shown in SEQ ID NO:1 or from nucleotide sequences obtained by hybridization of human cDNA with nucleotide sequences of SEQ ID NO:1. For identification of the mouse chromosome 2 central, the nucleotide probe is selected from the nucleotide sequence shown in SEQ ID NO:3. The nucleotide probes can be labeled, for example, with a radioactive, fluorescent, biotinylated, or chemiluminescent label, and detected by well known methods appropriate for the particular label selected.

Protocols for hybridizing nucleotide probes to preparations of metaphase chromosomes are well known in the art. A nucleotide probe will hybridize specifically to nucleotide sequences in the chromosome preparations which are complementary to the nucleotide sequence of the probe. A probe which hybridizes specifically to human chromosome region 15q13 or to a central region of the mouse chromosome 2 hybridizes to nucleotide sequences present in the human or mouse deep orange gene and not to nucleotide sequences present in other human or mouse genes. A probes which hybridizes specifically to a deep orange gene provides a detection signal at least 5-, 10, or 20-fold higher than the background hybridization provided with non-deep orange coding sequences.

A human chromosome which specifically hybridizes to a human deep orange nucleotide probe is identified as a human chromosome 15. Preferably, the nucleotide probe identifies the long arm of human chromosome 15. More preferably, the nucleotide probe identifies a q13 region of human chromosome 15. A chromosome which specifically hybridizes to a mouse deep orange nucleotide probe is identified as a mouse chromosome 2. Preferably, the central region of mouse chromosome 2 is identified.

The invention provides a mammal which does not express an endogenous wild-type deep orange gene. The endogenous deep orange gene of such mammals is mutant such that a wild-type deep orange protein is not expressed. Methods of making mammals containing germline gene alterations ("transgenic mammals") are well known in the art. The mammal can be any experimental mammal, such as a mouse, rat, or rabbit; however, a mouse is preferred. The endogenous wild-type deep orange gene of the mammal can be deleted entirely, resulting in an absence of deep orange protein in the mammal. Alternatively, mutations such as deletions, insertions, missense substitutions, or inversions, can be introduced into the mammal's genome. Such mutations result in expression of truncated or otherwise aberrant forms of deep orange protein in the mammal. Preferably, the transgenic mammal does not express the endogenous wild-type deep orange gene in one or more of the following tissues: spleen, thymus, prostate, testis, ovary, small intestine, mucosal lining of the colon, heart, brain, placenta, liver, skeletal muscle, pancreas, lymph node, appendix, peripheral blood leukocytes, or bone marrow.

The transgenic mammals of the invention are useful as model systems for studying the effects of drugs in the absence of wild-type deep orange protein or in the presence of altered forms of the deep orange protein in the mammal. The transgenic mammals can also be used to develop therapeutic treatments for diseases which may be associated with alterations in deep orange gene expression, such as neoplasias, emphysema, platelet storage pool disease, pigmentation defects, and diseases which involve defects in vesicle sorting and elevated levels of lysosomal enzymes.

The present invention also provides a method to aid in the diagnosis or prognosis of cancer or emphysema in a mammal. A deep orange gene or its expression products can be compared between a tissue which is suspected of being diseased and a normal tissue of the mammal. The normal tissue can be any tissue of the mammal, especially those which express a deep orange gene including, but not limited to, spleen, thymus, prostate, testis, ovary, small intestine, mucosal lining of the colon, heart, brain, placenta, liver, skeletal muscle, pancreas, lymph node, appendix, peripheral blood leukocytes, and bone marrow. The tissue suspected of being diseased can be derived from a different tissue type of the mammal, but preferably it is derived from the same tissue type, for example an intestinal polyp or other abnormal growth.

A difference between the deep orange gene, mRNA, or protein in the two tissues which are compared, for example in molecular weight, amino acid or nucleotide sequence, or relative abundance, indicates a somatic mutation in the deep orange gene in the tissue of the mammal which was suspected of being diseased.

Deep orange genes in the two tissues can be compared by any means known in the art. For example, the two genes can be sequenced, and the sequence of the deep orange gene gene in the tissue suspected of being diseased can be compared with the wild-type sequence in the normal tissue. The deep orange genes or portions of the deep orange genes in the two tissues can be amplified, for example using nucleotide prime selected from the nucleotide sequences shown in SEQ ID NOS:1 and 3 in the polymerase chain reaction (PCR). The amplified genes or portions of genes can be hybridized to nucleotide probes selected from the nucleotide sequences shown in SEQ ID NOS:1 and 3. The nucleotide probes can be labeled by a variety of methods, such as radiolabeling, biotinylation, or labeling with fluorescent or chemiluminescent tags, and detected by standard methods known in the art.

Alternatively, deep orange mRNA in the two tissues can be compared. PolyA+RNA can be isolated from the two tissues as is known in the art. For example, one of skill in the art can readily determine differences in the size or amount of deep orange mRNA transcripts between the two tissues that are compared, using Northern blots and nucleotide probes selected from the nucleotide sequences shown in SEQ ID NOS:1 and 3.

Any method for analyzing proteins can be used to compare two deep orange proteins from matched samples. The sizes of the deep orange proteins in the two tissues can be compared, for example, using the antibodies of the present invention to detect deep orange proteins in Western blots of protein extracts from the two tissues. Other changes, such as expression levels and subcellular localization, can also be detected immunologically.

Similarly, a genetic predisposition to neoplasia or emphysema in a mammal can be detected by comparing a wild-type deep orange gene, mRNA, or protein with a deep orange gene, mRNA, or protein in a fetal tissue. Fetal tissues which can be used for this purpose include, but are not limited to, amniotic fluid, chorionic villi, blood, and the blastomere of an in vitro-fertilized embryo. The wild-type deep orange gene can be obtained from any tissue. The mRNA or protein can be obtained from a normal tissue of a mammal in which the deep orange gene is expressed. Such tissues are disclosed above. Differences such as alterations in the nucleotide sequence or size of the fetal deep orange gene or mRNA, or alterations in the molecular weight, amino acid sequence, or relative abundance of fetal deep orange protein indicate a germline mutation in the deep orange gene of the fetus which indicates a genetic predisposition to neoplasia or emphysema.

What is claimed is:

1. An isolated subgenomic polynucleotide comprising the nucleotide sequence shown in SEQ ID NO:3.

2. An isolated subgenomic polynucleotide comprising the nucleotide sequence shown in SEQ ID NO:1.

3. An isolated subgenomic polynucleotide comprising at least 2919 nucleotides and encoding an amino acid sequence which is at least 95% identical to the amino acid sequence shown in SEQ ID NO:4.

4. An isolated polynucleotide comprising a nucleic acid sequence with at least 95% identity to the nucleotide sequence shown in SEQ ID NO:3, or a sequence fully complementary thereto.

5. An expression construct for expressing deep orange protein comprising:
   a promoter; and
   a polynucleotide segment encoding a deep orange protein with the amino acid sequence shown in SEQ ID NO:4, wherein the polynucleotide segment is located downstream from the promoter and comprises SEQ ID NO:3, and wherein transcription of the polynucleotide segment initiates at the promoter.

6. An expression construct for expressing deep orange protein comprising:
   a promoter; and
   a polynucleotide segment comprising nucleic acid with 95% identity to SEQ ID NO:1 wherein said nucleic acid encodes human deep orange protein.

7. An expression construct comprising the subgenomic polynucleotide of claim 3.

8. An expression construct of claim 7, comprising a polynucleotide encoding deep orange protein with the amino acid sequence shown in SEQ ID NO:4.

9. An expression construct of claim 7 comprising a polynucleotide of SEQ ID NO:1.

10. A recombinant host cell comprising the expression construct of claim 7.

11. A recombinant host cell comprising the expression construct of claim 8.

12. A recombinant host cell comprising the expression construct of claim 9.

13. A recombinant method of producing a polypeptide, comprising culturing the recombinant host cell of claim 10 under conditions such that said polypeptide is expressed and recovering said polypeptide.

14. A recombinant method of producing a polypeptide, comprising culturing the recombinant host cell of claim 11 under conditions such that said polypeptide is expressed and recovering said polypeptide.

15. A recombinant method of producing a polypeptide, comprising culturing the recombinant host cell of claim 12 under conditions such that said polypeptide is expressed and recovering said polypeptide.

* * * * *